(12) United States Patent
Wilkison et al.

(10) Patent No.: US 7,078,230 B2
(45) Date of Patent: Jul. 18, 2006

(54) ADIPOSE TISSUE-DERIVED STROMAL CELL THAT EXPRESSES CHARACTERISTICS OF A NEURONAL CELL

(75) Inventors: William O. Wilkison, Bahama, NC (US); Jeffrey Gimble, Chapel Hill, NC (US)

(73) Assignee: Artecel, Inc., Baltimore, MD (US)

( * ) Notice: Subject to any disclaimer, the term of this patent is extended or adjusted under 35 U.S.C. 154(b) by 0 days.

(21) Appl. No.: 09/793,173

(22) Filed: Feb. 26, 2001

(65) Prior Publication Data

US 2001/0033834 A1  Oct. 25, 2001

Related U.S. Application Data

(60) Provisional application No. 60/185,338, filed on Feb. 26, 2000.

(51) Int. Cl.
*C12N 5/00* (2006.01)

(52) U.S. Cl. .................. 435/325; 435/375; 435/383

(58) Field of Classification Search ................ 435/325, 435/352, 363, 69.1, 93.1, 93.2, 93.7; 424/93.1, 424/93.2, 93.7
See application file for complete search history.

(56) References Cited

U.S. PATENT DOCUMENTS

| | | | |
|---|---|---|---|
| 5,041,138 A | 8/1991 | Vacanti et al. |
| 5,144,016 A | 9/1992 | Skjak-Braek et al. |
| 5,486,359 A | 1/1996 | Caplan et al. |
| 5,516,532 A | 5/1996 | Atala et al. |
| 5,536,656 A | 7/1996 | Kemp et al. |
| 5,709,854 A | 1/1998 | Griffith-Cima et al. |
| 5,723,331 A | 3/1998 | Tubo et al. |
| 5,736,372 A | 4/1998 | Vacanti et al. |
| 5,736,396 A | 4/1998 | Bruder et al. |
| 5,741,685 A | 4/1998 | Vacanti |
| 5,759,830 A | 6/1998 | Vacanti et al. |
| 5,770,193 A | 6/1998 | Vacanti et al. |
| 5,770,417 A | 6/1998 | Vacanti et al. |
| 5,786,207 A | 7/1998 | Katz et al. |
| 5,804,178 A | 9/1998 | Vacanti et al. |
| 5,811,094 A | 9/1998 | Caplan et al. |
| 5,827,735 A | 10/1998 | Young et al. |
| 5,855,610 A | 1/1999 | Vacanti et al. |
| 5,863,531 A | 1/1999 | Naughton et al. |
| 5,879,940 A | 3/1999 | Torok-Storb et al. |
| 5,902,741 A | 5/1999 | Purchio et al. |
| 5,908,784 A | 6/1999 | Johnstone et al. |
| 5,942,225 A | 8/1999 | Bruder et al. |
| 5,944,754 A | 8/1999 | Vacanti |
| 6,027,744 A | 2/2000 | Vacanti et al. |
| 6,030,836 A | 2/2000 | Thiede et al. |
| 6,103,522 A | 8/2000 | Torok-Storb et al. |
| 6,123,727 A | 9/2000 | Vacanti et al. |
| 6,139,574 A | 10/2000 | Vacanti et al. |
| 6,143,501 A | 11/2000 | Sittinger et al. |
| 6,153,432 A | 11/2000 | Halvorsen et al. |
| 6,200,606 B1 | 3/2001 | Peterson et al. |
| 6,391,297 B1 | 5/2002 | Halvorsen |
| 6,429,013 B1 | 8/2002 | Halvorsen et al. |

FOREIGN PATENT DOCUMENTS

| | | |
|---|---|---|
| WO | WO 96/02662 A1 | 2/1996 |
| WO | WO 98/20731 A1 | 5/1998 |
| WO | WO 99/28444 A1 | 6/1999 |
| WO | WO 99/43286 A2 | 9/1999 |
| WO | WO 99/61587 A1 | 12/1999 |
| WO | WO 00/44882 A2 | 8/2000 |
| WO | WO 00/53795 A1 | 9/2000 |
| WO | WO 01/21767 A2 | 3/2001 |

OTHER PUBLICATIONS

Kim et al. Effect of partial hepatectomy on in vivo engraftment after intravenous administration of human adipose tissue stroma cells in mouse. Microsurgery 23:424-431, 2003.*

Halliday et al. Alzheimer's disease and inflammation: a review of cellular and therapeutic mechanisms. Clin Exp Pharmacol Physiol 27: 1-8, 2000.*

Feigin et al. Recent advances in Huntington's disease: implication for experimental therapeutics. Curr Opin Neurol 15: 483-489. 2002.*

Steece-Collier et al. Etiology of Parkinson's disease: genetics and environment revisited. Proc Natl Acad Sci USA 99(22): 13972-13974, 2002.*

(Continued)

*Primary Examiner*—Elizabeth Kemmerer
*Assistant Examiner*—Bridget E. Bunner
(74) *Attorney, Agent, or Firm*—Drinker Biddle & Reath, LLP

(57) ABSTRACT

The invention is in the area of pleuripotent stem cells generated from adipose tissue-derived stromal cells and uses thereof. In particular, the invention includes isolated adipose tissue derived stromal cells that have been induced to express at least one phenotypic characteristic of a neuronal, astroglial, hematopoietic progenitor, or hepatic cell. The invention also includes an isolated adipocyte tissue-derived stromal cell that has been dedifferentiated such that there is an absence of adipocyte phenotypic markers.

2 Claims, No Drawings

OTHER PUBLICATIONS

Yang et al. Adipose tissue-derived stromal cells express neuronal phenotypes. Chin Med J 116(3): 425-429, 2004.*
Safford et al. Characterization of neuronal/glial differentiation of murine adipose-derived adult stromal cells. Exp Neurol 187: 319-328, 2004.*
Kang et al. Neurogenesis of rhesus adipose stromal cells. J Cell Sci 117: 4289-4299, 2004.*
Kang et al. Improvement of neurological deficits by intracerebral transplantation of human adipose tissue-derived stromal cells after cerebral ischemia in rats. Exp Neurol 183: 355-366, 2003.*
Erikson, G et al. Chondrogenic Potential of Adipose Tissue-Derived Stromal Cells in Vitro and in Vivo. Biochem Biophys Res Comm 290(2): 763-769, 2002.*
Halvorsen et al. Thiazolidinediones and glucocorticoids synergistically induce differentiation of human adipose tissue stromal cells: biochemical, cellular, and molecular analysis. Metabolism. 50(4):407-413, 2001.*
Halvorsen et al. Adipose-derived stromal cells—their utility and potential in bone formation. Int J Obes Relat Metab Disord. Suppl 4:S41-44, 2000.*
Halvorsen et al. Extracellular matrix mineralization and osteoblast gene expression by human adipose tissue-derived stromal cells. Tissue Eng. 7(6):729-741, 2001.*
Zuk Pa et al. Human adipose tissue is a source of multipotent stem cells. Mol Biol Cell. 13(12):4279-4295, 2002.*
Safford et al. Neurogenic differentiation of murine and human adipose-derived stromal cells. Biochem Biophys Res Commun. 294(2):371-379, 2002.*
Sen A et al. Adipogenic potential of human adipose derived stromal cells from multiple donors is heterogeneous. J Cell Biochem. 81(2):312-319, 2001.*
Burris et al., *A Novel Method for Analysis of Nuclear Receptor Function at Natural Promoters: Peroxisome Proliferator-Activated Receptor γ Agonist Actions on a P2 Gene Expression Detected Using Branched DNA Messenger RNA Quantitation, Molecular Endocrinology*, 1999, 13, 3, 410.
Gimble, Jeffrey Martin, *The Function of Adipocytes in the Bone Marrow Stroma, The New Biologist*, 1990, 2, 4, 304.
Gimble et al., *Nuclear Hormone Receptors and Adipogenesis, Critical Reviews in Eukaryotic Gene Expression*, 1998, 8(2), 141.
Gimble et al., *Adipocyte Biology of the Bone, Adipocyte Biology and Hormone Signaling*, IOS Press, The Netherlands, 2000, 231.
Gronthos et al., *Surface Protein Characterization of Human Adipose Tissue-Derived Stromal Cells, Journal of Cellular Physiology*, 2001, 9999, 1.
Mizuno, M.D., Hiroshi, *The Myogenic Potential of Human Processed Lipoaspirates—Part I: Morphological, immunohistochemical analysis and gene expression, J. Jpn. P.R.S.*, 2001, 21, 427.
Mizuno et al., *Myogenic Differentiation by Human Processed Lipoaspirate Cells, Plastic and Reconstructive Surgery* 2002, 109, 1, 199.
Saladin et al., *Differential Regulation of Peroxisome Proliferator Activated Receptor γ1 (PPARγ1) and PPARγ2 Messenger RNA Expression in the Early Stages of Adipogenesis[1], Cell Growth & Differentiation*, 1999, 10, 43.
Zuk et al., *Multilineage Cells from Human Adipose Tissue: Implications for Cell-Based Therapies, Tissue Engineering*, 2001, 7, 2, 211.

Bain et al., "Embryonic Stem Cells Express neuronal Properties in Vitro," *Develop. Biol.*, 168:342-357.
Beresford et al., "Evidence for an inverse relationship between the differentiation of adipocytic and osteogenic cells in rat marrow stormal cell cultures," *J. Cell Sci.*, (1992), 99:131.
Bjornson, "Turning Brain into Blood: A Hematopoietic Fate Adopted by Adult Neural Stem Cells in Vivo," *Science*, (1999), 283:534-537.
Bruder et al., "Mesenchymal Stem Cells in Bone Development, Bone Repair, and Skeletal Regeneration Therapy," *J. Cell Biochem.*, (1994), 56:283-294.
Dani et al., "Differentiation of embryonic stem cells into adipocytes in vitro," *J. Cell Sci.*, (1997) 110:1279-1285.
Dorheim et al., "Osteoblastic Gene Expression During Adiopogensis in Hematopoietic Supporting Murine Bone Marrow Stromal Cells," *J. Cell. Physiol.*, (1993), 154:317-328.
Gimble et al., "Adipogensis in a murine bone marrow stromal cell line capable of supporting B lineage lymphocyte growth and proliferation: biochemical and molecular characterization," *Eur. J. Immunol.*, (1990), 20:379-387.
Gimble et al., "Characterization of Murine Bone Marrow and Spleen-Derived Stromal Cells: Analysis of Leukocyte Marker and Growth Factor mRNA transcript Levels," *Blood*, (1989) 74:303-311.
Gimble et al., "The Function of Adipocytes in the Bone Marrow Stromal: An Update," *Bone*, (1996), 19:421-428.
Gronthos et al., "The STRO-1+ Fraction of Adult Human Bone Marrow Contains the Osteogenic Precursors," *Blood*, (1994), 84:4164-4173.
Jakoby & Pastan, "Basic Methods" and "Media and Growth Requirements," *Methods in Enzymology, Cell Culture*, vol. LVIII, pp. 62-72.
Jackson et al., "Hematopoietic potential of stem cells isolated from murine skeletal muscle," *PNAS*, (1999), 96:14482-14486.
Johnson RS, "Targeting of Nonexpressed Genes in Embryonic Stem Cells Via Homologous Recombination," *Science*, (1989), 245:1234-1236.
Kopen et al., "Marrow stromal cells migrate throughout forebrain and cerebellum, and they differentiate into astrocytes after injection into neonatal mouse brains," *PNAS*, (1999), 96:10711-10716.
Lee et al., "Normal B Cell Precursors Responsive To Recombinant Murine IL-7 and Inhibition of IL-7 Activity by Transforming Growth Factor-$\beta^1$," *J. Immunol.*, (1989), 142:3875-3883.
McDonald et al., "Trasnplanted embryonic stem cells survive, differentiate and promote recovery in injured rat spinal cord," *Nature Med.*, (1999), 5(12):1410-1412.
Medina et al., "Suppression of B Lymphopoeisis during Normal Pregnancy," *J. Exp. Med.*, (1993), 178:1507-1515.
Moore et al., "In Vitro Colony Formation by Normal and Leukemic Human Hematopoietic Cells: characterizaiton of the Colony-Forming Cells[1,2]," *J. Natl. Cancer Inst.*, (1973), 50:603-623.
O'Shea KS, "Embryonic Stem Cell Models of Development," *Anat. Rec.*, (1999) 257:32-41.
Petersen et al., "Bone Marrow as a Potential Source of Hepatic Oval Cells," *Science*, (1999), 284:1168-1170.
Pereira et al., "Marrow stromal cells as a source of progenitor cells for nonhematopoietic tissues in transgenic mice with a phenotype of ostegenesis imperfecta," *PNAS*, (1998), 95:1142-1147.

Pietrangeli et al., "Stromal cell lines which support lumphocyte growth: characterization, sensitivity to radiation and responsiveness to growth factors," *Eur. J. Immunol.*, (1988), 18:863-872.

Proctop, "Marrow Stromal Cells as Stem Cells for Continual Renewal of Nonhematopoietic Tissues and as Potential Vectors for Gene Therapy," *J Cell Biochem Suppl.*, (1998), 30-31:284-285.

Quesenberry et al., "Correlates between Hematopoiesis and Neuropoiesis: Neural Stem Cells," *J Neurotrauma*, (1999), 16:661-666.

Remoncourt et al., "Neurons derived in vitro from ES cells express homeoproteins characteristic of motoneurons and interneurons," *Mech. Dev.*, (1998) 79:185-197.

Sanchez-Ramos et al., "Adult Bone Marrow stromal cells differentiate into Neural Cells in Vitro," *Exp Neurology*, (2000), 164:247-256.

Svendson & Smith, "New prospects for human stem-cell therapy in the nervous system," *Trends Neurosci*, (1999), 22:357-364.

Till & McCuloch, "A Direct Measurement of the Radiation sensitivity of Normal Mouse Bone Marrow Cells[1]," *Rad. Res.*, (1961), 14:213-222.

Trentin, "Transplantation: The State of the Art," *Cardiovasc. Res. Cent. Bull*, (1965), 4:38-44.

Woodbury et al., "Adult Rat and Human Bone Marrow Stromal Cells Differentiate Into Neurons," *J Neuroscience Research*, (2000), 61:364-370.

Darmon, et al., "5-Azacytidine Is Able To Induce The Conversion Of Teratocarcinoma-Derived Mesenchymal Cells Into Epithelial Cells," *The IMBO Journal*, vol. 3, No. 5, 1984, pp. 961-967.

\* cited by examiner

ADIPOSE TISSUE-DERIVED STROMAL CELL THAT EXPRESSES CHARACTERISTICS OF A NEURONAL CELL

PRIOR APPLICATION

This application claims priority to U.S. Ser. No. 60/185,338, filed on Feb. 26, 2000.

FIELD OF THE INVENTION

The invention is in the area of pleuripotent stem cells generated from adipose tissue-derived stromal cells and uses thereof. In particular, the invention includes isolated adipose tissue derived stromal cells that have been induced to express at least one phenotypic characteristic of a neuronal, astroglial, hematopoietic progenitor, or hepatic cell. The invention also includes an isolated adipocyte tissue-derived stromal cell that has been dedifferentiated such that there is an absence of adipocyte phenotypic markers.

BACKGROUND OF THE INVENTION

A stem cell must meet the following criteria: (1) ability of a conal stem cell population to self-renew; (2) ability of a clonal stem cell population to generate a new, terminally differentiated cell type in vitro; (3) Ability of a clonal stem cell population to replace an absent terminally differentiated cell population when transplanted into an animal depleted of its own natural cells.

The neonatal period in human development is characterized by the presence of "stem" cells with the potential to develop along multiple differentiation pathways. The terminal differentiation of these cells is determined by cytokine and hormonal cues which co-ordinate organogenesis and tissue architecture. Murine embryonic stem (ES) cells have been isolated and studied extensively in vitro and in vivo. Using exogenous stimuli in vitro, investigators have induced ES cell differentiation along multiple lineage pathways. These pathways include neuronal, B lineage lymphoid, and adipocytes (Dani et al. (1997) *J. Cell Sci.* 110:1279; Remoncourt et al. (1998) *Mech Dev* 79:185; O'Shea, S. (1999) *Anat. Rec.* 257:32, 1999). The ES cells have been manipulated in vivo by homologous recombination techniques to generate gene specific null or "knock-out" mice (Johnson, R. S. (1989) *Science* 245:1234). Once ES cell clones lacking a specific gene are isolated, they are transplanted into a fertilized murine zygote. The progeny of this isolated ES cell can develop into any and all murine tissues in a coordinated manner.

Multipotential stem cells exist in tissues of the adult organism. The best characterized example of a "stem cell" is the hematopoietic progenitor isolated from the bone marrow and peripheral blood. Seminal studies by Trentin and colleagues (Trentin (1965) *Cardiovasc. Res. Cent. Bull* 4:38; Till & McCulloch (1961) *Rad. Res.* 14:213) examined lethally irradiated mice. In the absence of treatment, these animals died because they failed to replenish their circulating blood cells; however, transplantation of bone marrow cells from syngeneic donor animals rescued the host animal. The donor cells were responsible for repopulating all of the circulating blood cells. A wealth of elegant studies have gone on to demonstrate that donation of a finite number of undifferentiated hematopoietic stem cells is capable of regenerating each of the eight or more different blood cell lineages in a host animal. This work has provided the basis for bone marrow transplantation, a widely accepted therapeutic modality for cancer and inborn errors of metabolism. Thus, hematopoietic stem cells remain present in normal human bone marrow throughout life; they are not limited to the neonatal period.

There is exciting new evidence that hematopoietic progenitors may not be limited to the bone marrow microenvironment. Investigators at the University of Calgary have examined neuronal stem cells, which routinely differentiate along neuronal cell lineage pathways. When these cells were transplanted into lethally irradiated hosts, the investigators detected the presence of donor cell markers in newly produced myeloid and lymphoid cells (Bjornson (1999) *Science* 283:534). Investigators at the Baylor College of Medicine have performed similar studies using satellite cells isolated from murine skeletal muscle (Jackson et al. (1999) *PNAS* 96:14482). When these muscle-derived cells were transplanted into lethally irradiated hosts, the investigators detected the presence of the muscle gene markers in all blood cell lineages. Together, these studies indicate that neuronal and muscle tissues contain stem cells capable of hematopoietic differentiation. This suggest that sites other than the bone marrow may provide a renewable source of hematopoietic progenitors with potential application to human disease therapy (Quesenberry et al. (1999) *J. Neurotrauma* 16:661: Scheffler et al. (1999) *Trends Neurosci* 22:348; Svendson & Smith (1999) *Trends Neurosci* 22:357).

Just as neuronal and muscle cells are capable of regenerating the irradiated bone marrow, bone marrow derived cells are capable of repopulating other organ sites. When bone marrow derived hematopoietic and stromal cells are transplanted into an animal with an injured liver, they are capable of regenerating hepatic oval cells in the host animal (Peterse et al. (1999) *Science* 284:1168). Similarly, when labeled bone marrow stromal cells are implanted into the lateral ventricle of a neonatal mouse, they were capable of differentiating into mature astrocytes (Kopen et al. (1999) *PNAS* 96:10711). Indeed, when bone marrow stromal cells are transplanted intraperitoneally into mice, they are detected throughout the organs of the host animal, including the spleen, lung, bone marrow, bone, cartilage, and skin (Pereira et al (1998) *PNAS* 95:p 1142, 1998). These studies suggest that the bone marrow stromal cell is capable of differentiating into lineages different from their original dermal origin (Kopen et a. (1999) *PNAS* 96:10711).

The recent development of entire organisms from a single donor cell is consistent with this hypothesis. For example, the "Dolly" experiment showed that cells isolated from an ovine mammary gland could develop into a mature sheep. In similar murine studies, cells derived from the corpus luteum of the ovary could develop into a mature mouse. These studies suggest that stem cells with ability to differentiate into any and all cell types continue to exist in the adult organism. Thus, "embryonic" stem cells may be retained throughout the life of an individual.

The adult bone marrow microenvironment is the potential source for these hypothetical stem cells. Cells isolated from the adult marrow are referred to by a variety of names, including stromal cells, stromal stem cells, mesenchymal stem cells (MSCs), mesenchymal fibroblasts, reticular-endothelial cells, and Westen-Bainton cells (Gimble et al. (1996) *Bone* 19:421, 1996). In vitro studies have determined that these cells can differentiate along multiple mesenchymal or mesodermal lineages which include, but are not limited to, adipocytes (fat cells) (Gimble et al. (1990) *Eur J. Immunol* 20:379), Chondrocytes (Bruder et al. (1994) *J. Cell Biochem.* 56:283), hematopoietic supporting cells (Pietrangeli et al. (1988) *Eur. J. Immunol.* 18:863), skeletal muscle myocytes (Prockop (1998) *J. Cell Biochem Suppl.* 30–31:284–5), smooth muscle myocytes (Charbord), and osteoblasts (Beresford et al. (1992) *J. Cell Sci.* 99:131; Dorheim et al. (1993) *J. Cell Physiol.* 154:317). In addition, bone marrow stromal cells display the ability to differentiate into astrocytes (Kopen et al. (1999) *PNAS* 96:10711) and hepatic oval cells (Petersen et al. (1999) *Science* 284:1168). Based on these findings, the bone marrow has been proposed as a source of stromal stem cells for regeneration of bone, cartilage, muscle, adipose tissue, liver, neuronal, and other tissues. However, extraction of bone marrow stromal cells presents a high level of risk and discomfort to the patient.

In contrast, adult human extramedullary adipose tissue-derived stromal cells represent a stromal stem cell source that can be harvested routinely with minimal risk or discomfort to the patient. Pathologic evidence suggests that adipose-derived stromal cells are capable of differentiation along multiple lineage pathways. The most common soft tissue tumors, liposarcomas, develop from adipocyte-like cells. Soft tissue tumors of mixed origin are relatively common. These tumors may include elements of adipose tissue, muscle (smooth or skeletal), cartilage, and/or bone. In patients with a rare condition known as progressive osseous heteroplasia, subcutaneous adipocytes form bone for unknown reasons.

Recent studies have demonstrated the specific ability of bone marrow-derived stromal cells to undergo neuronal differentiation in vitro (Woodbury et al. (2000) *J Neuroscience Research* 61:364; Sanchez-Ramos et al. (2000) *Exp Neurology* 164:247). In these investigations, treatment of bone marrow stromal cells with antioxidants, epidermal growth factor (EGF), or brain derived neurotrophic factor (BDNF) induced the cells to undergo morphologic changes consistent with neuronal differentiation, i.e., the extension of long cell processes terminating in growth cones and filopodia (Woodbury et al. (2000) *J Neuroscience Research* 61:364; Sanchez-Ramos et al. (2000) *Exp Neurology* 164:247). In addition, these agents induced the expression of neuronal specific protein including nestin, neuron-specific enolase (NSE), neurofilament M (NF-M), NeuN, and the nerve growth factor receptor trkA (Woodbury et al. (2000) *J Neuroscience Research* 61:364; Sanchez-Ramos et al. (2000) *Exp Neurology* 164:247

U.S. Pat. No. 5,486,359 to Osiris is directed to an isolated, homogeneous population of human mesenchymal stem cells which can differentiate into cells of more than one connective tissue type. The patent discloses a process for isolating, purifying, and greatly replicating these cells in culture, i.e. in vitro.

U.S. Pat. No. 5,942,225 to Case Western and Osiris describes a composition for inducing lineage-directed differentiation of isolated human mesenchymal stem cells into a single particular mesenchymal lineage, which includes human mesenchymal stem cells and one or more bioactive factors for inducing differentiation of the mesenchymal stem cells into a single particular lineage.

U.S. Pat. No. 5,736,396 to Case Western describes a method of inducing ex vivo lineage-directed differentiation of isolated human mesenchymal stem cells which includes contacting the mesenchymal stem cells with a bioactive factor so as to thereby induce ex vivo differentiation thereof into a single particular mesenchymal lineage. The patent also describes method of treating an individual in need of mesenchymal cells of a particular mesenchymal lineage which includes administering to an individual in need thereof a composition comprising isolated, human mesenchymal stem cells which have been induced to differentiate ex vivo by contact with a bioactive factor so as to thereby induce ex vivo differentiation of such cells into a single particular mesenchymal lineage.

U.S. Pat. No. 5,908,784 to Case Western discloses a composition for the in vitro chondrogenesis of human mesenchymal precursor cells and the in vitro formation of human chondrocytes therefrom, which composition includes isolated human mesenchymal stem cells condensed into close proximity as a packed cell pellet and at least one chondroinductive agent in contact therewith. The patent also describes a process for inducing chondrogenesis in mesenchymal stem cells by contacting mesenchymal stem cells with a chondroinductive agent in vitro wherein the stem cells are condensed into close proximity as a packed cell pellet.

U.S. Pat. No. 5,902,741 to Advanced Tissue Sciences, Inc. discloses a living cartilage tissue prepared in vitro, that includes cartilage-producing stromal cells and connective tissue proteins naturally secreted by the stromal cells attached to and substantially enveloping a three-dimensional framework composed of a biocompatible, non-living material formed into a three-dimensional structure having interstitial spaces bridged by the stromal cells. The patent also discloses a composition for growing new cartilage comprising mesenchymal stem cells in a polymeric carrier suitable for proliferation and differentiation of the cells into cartilage.

U.S. Pat. No. 5,863,531 to Advanced Tissue Sciences, Inc. discloses a tubular living stromal tissue prepared in vitro, comprising stromal cells and connective tissue proteins naturally secreted by the stromal cells attached to and substantially enveloping a three-dimensional tubular framework composed of a biocompatible, non-living material having interstitial spaces bridged by the stromal cells.

U.S. Pat. No. 5,811,094 to Osiris describes a method of producing a connective tissue which includes producing connective tissue in an individual in need thereof by administering to said individual a cell preparation containing human mesenchymal stem cells which is recovered from human bone marrow and which is substantially free of blood cells.

U.S. Pat. No. 6,030,836 describes a method of maintaining human hematopoietic stem cells in vitro comprising co-culturing human mesenchymal stem cells with the hematopoietic stem cells such that at least some of the hematopoietic stem cells maintain their stem cell phenotype.

U.S. Pat. No. 6,103,522 describes an irradiated immortalized human stromal cell line in a combined in vitro culture with human hematopoietic precursor cells.

WO 9602662A1 and U.S. Pat. No. 5,879,940 describes human bone marrow stromal cell lines that sustain hematopoiesis U.S. Pat. No. 5,827,735 to Morphogen describes purified pleuripotent mesenchymal stem cells, which are substantially free of multinucleated myogenic lineage-committed cells, and which are predominantly stellate-shaped, wherein the mesenchymal stem cells form predominantly fibroblastic cells when contacted with muscle morphogenic protein in tissue culture medium containing 10% fetal calf serum and form predominantly branched multinucleated structures that spontaneously contract when contacted with muscle morphogenic protein and scar inhibitory factor in tissue culture with medium containing 10% fetal calf serum.

WO 99/94328 describes the use of mesenchymal stem cells to treat the central nervous system and a method of directing differentiation of bone marrow stromal cells.

WO 98/20731 to Osiris describes a mesenchymal megakaryocyte precursor composition and method of isolating MSCs associated with isolated megakaryocytes by isolating megakaryocytes.

WO 99/61587 to Osiris describes human CD45 and/or fibroblast and mesenchymal stem cells.

WO 00/53795 to the University of Pittsburgh and The Regents of the University of California discloses adipose-derived stem cells and lattices substantially free of adipocytes and red blood cells and clonal populations of connective tissue stem cells. The cells can be employed, alone or within biologically-compatible compositions, to generate differentiated tissues and structures, both in vivo and in vitro. Additionally, the cells can be expanded and cultured to produce hormones and to provide conditioned culture media for supporting the growth and expansion of other cell populations. In another aspect, WO 00/53795 a lipo-derived lattice substantially devoid of cells, which includes extracellular matrix material form adipose tissue. The lattice can be used as a substrate to facilitate the growth and differentiation of cells, whether in vivo or in vitro, into anlagen or mature tissue or structures. WO 00/53795 did not disclose adipose tissue derived stromal cells that have been induced to express at least one phenotypic characteristic of a neuronal, astroglial, hematopoietic progenitor, or hepatic cell in its priority document, nor did it disclose an isolated adipocyte tissue-derived stromal cell that has been dedifferentiated such that there is an absence of adipocyte phenotypic markers.

WO 99/28444 discloses methods and compositions for differentiating stromal cells form adipose tissue into cells having osteoblastic properties, and methods for improving a subject's bone structure.

WO 00/44882 discloses a method and composition for inducing stromal cells derived from adipose tissue into fully functional pleuripotent stem cells as evidenced by differentiated hematopoietic or blood cell lineages, neuronal lineages, epithelial lineages, and uses thereof.

It is a goal of the present invention to provide new cells and methods for therapeutic treatment, diagnosis, other medical uses, and other purposes, including the cellular production of desired materials.

SUMMARY OF THE INVENTION

The present invention includes an isolated adipose tissue derived stromal cell that has been induced to express at least one characteristic of a neuronal cell, an astroglial cell, a hematopoietic progenitor cell, or a hepatic cell. These cells can be used therapeutically to autologously or allogeneically treat a host in need thereof, or for diagnostic purposes. The cells can be administered, for example, in any pharmaceutically acceptable carrier, including phosphate buffered saline, to the target area. Alternatively, the cells can be administered in a matrix, lattice, or other materials lending two or three dimensional structures to form a structured depo, for example, an implant or a graft. The three dimensional framework can be biodegradable or nonbiodegradable. Examples of biodegradable materials for use in administering these cells include alginate, polylactic acid, polyglycolic acid, polylactide-co-glycolide, proteins such as proteoglycans, glycoproteins, hyaluronins, fibronectins, and collagens. The cells can be administered, if desired, in combination with another agent such as a cytokine, growth factor, chemical inducing agent, biologic, chemotherapeutic, hormone, other cell, protein, carbohydrate, peptide, or nucleic acid.

In a preferred aspect of the invention, stromal cells are derived from subcutaneous, mammary, gonadal, or omental adipose tissues and de-differentiated into fully functional pleuripotent stem cells capable of being partially or completely differentiated into hematopoietic or blood cell lineages, neuronal (nervous system) lineages, astroglial cells, hepatic cells or epithelial lineages. The invention also provides methods of using the induced adipose tissue derived cells therapeutically (for example, in tissue repair, regeneration, reconstruction or enhancement, diagnostically), as bioreactors to produce desired substances, and in genetic and tissue engineering.

The invention provides methods and compositions for the isolation, characterization, and differentiation of adult human extramedullary adipose tissue-derived stromal stem cells along non-mesenchymal lineages, including but not limited to, hematopoietic cells and neuronal cells, and outlines their use as pleuripotent stem cells for the treatment of a number of human and animal conditions and diseases.

In another aspect of the invention, a method for inducing adipose-tissue derived stromal cells to express at least one characteristic of a non-adipose tissue derived cell, for example, a neuronal, astroglial, hematopoietic progenitor, or hepatic cell, is provided comprising: culturing isolated adipose tissue-derived stromal cells in a chemically defined culture medium that optionally contains serum and appropriate growth factors, hormones, cytokines, serum factors, embryonic extracts, preferably a non-human embryonic extract; and/or chemical compounds to induce specific lineage differentiation.

The methods and compositions of the invention can be used for autologous and allogeneic transplantation of cells for the treatment of human conditions, including but not limited to, blood dyscrasias, cancer, central nervous diseases and trauma, peripheral nervous diseases and trauma, liver diseases and trauma, among others.

In addition, the cells of the present invention can be genetically modified to express a therapeutic gene product. The adipose-derived cells can be genetically modified, e.g., to express exogenous genes or to repress the expression of endogenous genes. In accordance with this embodiment, the cell is exposed to a gene transfer vector comprising a nucleic acid including a transgene, such that the nucleic acid is introduced into the cell under conditions appropriate for the transgene to be expressed within the cell. The transgene generally is an expression cassette, including a coding polynucleotide operably linked to a suitable promoter. The coding polynucleotide can encode a protein, or it can encode biologically active RNA, such as antisene RNA or a ribozyme.

DETAILED DESCRIPTION OF THE INVENTION

The invention provides methods and compositions for adipose tissue-derived stromal cells induced to express at least one characteristic of a non-adipose tissue derived cell, preferably a neuronal, astroglial, hepatic or hematopoietic progenitor cell. The cells produced by the methods of invention can provide a source of partially or fully differentiated, functional cells having characteristics from multiple tissue lineages for research, transplantation, and development of tissue engineering products for the treatment of animal disease, preferably human disease, and tissue repair or improvement.

Adipose tissue offers a potential alternative to bone marrow as a source of multipotential stromal stem cells. Adipose tissue is readily accessible and abundant in many individuals. Obesity is a condition of epidemic proportions in the United States, where over 50% of adults exceed the recommended body mass index (BMI) based on their height and weight. Adipocytes can be harvested by liposuction on an outpatient basis. Liposuction is a relatively non-invasive procedure with cosmetic effects, which are acceptable to the vast majority of patients. It is well documented that adipocytes are a replenishable cell population. Even after surgical removal by liposuction or other procedures, it is common to see a recurrence of adipocytes in an individual over time at the same site. This suggests that adipose tissue contain cells that are capable of producing new adipose cells.

In one embodiment of the invention, an adipose tissue derived stromal cell induced to express at least one phenotypic characteristic of a neuronal, astroglial, hepatic or hematopoietic progenitor cell is provided. Phenotypic markers of the desired cells are well known to those of ordinary skill in the art, and copiously published in the literature. Additional phenotypic markers continue to be disclosed or can be identified without undue experimentation. Any of these markers can be used to confirm that the adipose cell has been induced to a differentiated state. Lineage specific phenotypic characteristics can include cell surface proteins, cytoskeletal proteins, cell morphology, and secretory products. Neuronal characteristics include the expression of neuronal markers such as NeuN, NF-M, NSE, nestin, and trkA. Blood specific markers can include the presence of CD4, CD8, CD7, CD19, CD45, CD33, CD34, TCR, etc. One of ordinary skill in the art will recognize that known calorimetric, fluorescent, immunochemical, polymerase chain reaction, chemical or radiochemical methods can readily ascertain the presence or absence of a lineage specific marker.

In another embodiment, the invention provides a dedifferentiated, isolated, adipose tissue derived stromal cell capable of being induced to express at least one characteristic of a non-adipose tissue derived cell, for example, neuronal, astroglial, hepatic or hematopoietic progenitor cell. A dedifferentiated adipose derived stromal cell can be identified by the absence of adipocyte markers. In another embodiment the dedifferentiated adipocyte can be provided in combination with a pharmaceutically acceptable carrier for a therapeutic application, including but not limited to tissue repair, regeneration, reconstruction or enhancement. Adipose tissue derived stromal cells can be cultured by the methods disclosed herein to dedifferentiate the stromal cells such that the dedifferentiated stromal cells can then be induced to express characteristics of cells other than adipose tissue derived cells. The dedifferentiated adipocyte can be modified to include a non-endogenous gene sequence for production of a desired protein or peptide. The dedifferentiated adipocyte can, in an alternative embodiment, be administered to a host in a two or three dimensional framework for a desired therapeutic purpose.

In another embodiment of the invention, a method is provided for differentiating adipose tissue-derived stromal cells into cells having the properties of hematopoietic stem cells, neuronal cells, astroglial, hepatic or other lineages, comprising: plating isolated adipose tissue-derived stromal cells at a desired density, including but not limited to a density of about 1,000 to about 500,000 cells/cm$^2$; incubating the cells in a chemically defined culture medium comprising at least one compound selected from the group consisting of: growth factor, hormone, cytokine and serum factor; and optionally, an embryonic extract, preferably a non-human embryonic extract. In another embodiment, the cell is differentiated in the absence of serum but in the presence of a chemical agent, for example, an oxidizing agent such as 2-mercaptoethanol.

In another embodiment, the invention provides a method for inducing an isolated adipose tissue-derived stromal cell to express at least one characteristic of a cell of non-mesenchymal lineage, comprising: plating isolated adipose tissue-derived stromal cell to a useful density, including but not limited to a density of about 1,000 to about 500,000 cells/cm$^2$; incubating the cells in a chemically defined culture medium at least one compound selected from the group consisting of: growth factors, hormones, cytokines and serum factors; and optionally, an embryonic extract, preferably a non-human embryonic extract.

In still another embodiment, the invention provides adipose-derived dedifferentiated cells, pleuripotent stem cells and differentiated cells of nonmesenchymal lineages that are produced according to the methods of the invention. Such cells are useful in autologous and allogenic transplantations.

In one preferred embodiment, the site is central nervous system tissue and the desired characteristic or phenotype is neuronal. In a second preferred embodiment, the site is central nervous system tissue and the desired characteristic or phenotype is astroglial. In another preferred embodiment, the site is intravenous and the desired characteristic or cell type is hematopoietic. In yet another embodiment, the site is the hepatic system, and in particular, the liver, and the desired characteristic or phenotype is hepatic. Preferably, the subject is mammalian, more preferably the subject is human.

In yet another embodiment, the invention provides a method of improving hematopoiesis in a patient, comprising transplantation of the cells of the invention into the patient. Preferably, the transplantation is by intravenous infusion. In one embodiment, the cell is transiently or stably transfected with at least one nucleic acid sequence. A viral or other vehicle containing at least one desired nucleic acid sequence to be introduced into the cell may mediate transfection.

The adipose tissue derive stromal cells useful in the methods of invention may be isolated by a variety of methods known to those skilled in the art. For example, such methods are described in U.S. Pat. No. 6,153,432 incorporated herein in its entirety. In a preferred method, adipose tissue is isolated from a mammalian subject, preferably a human subject. A preferred source of adipose tissue is omental adipose. In humans, the adipose is typically isolated by liposuction. If the cells of the invention are to be transplanted into a human subject, it is preferable that the adipose tissue be isolated from that same subject so as to provide for an autologous transplant. Alternatively, the administered tissue may be allogenic.

In one method of isolating adipose tissue derived stromal cells, the adipose tissue is treated with collagenase at concentrations between 0.01 to 0.5%, preferably 0.04 to 0.2%, most preferably about 0.1%, trypsin at concentrations between 0.01 to 0.5%, preferably 0.04%, most preferably about 0.2%; and/or dispase at concentrations of 0.5 ng/ml to 10 ng/ml; and/or effective concentrations of hyaluronidase or Dnase; and ethylenediaminetetra-acetic acid (EDTA) at concentrations of about 0.01 to 2.0 mM, preferably at about 0.1 to about 1.0 mM, most preferably at 0.53 mM; at temperatures between 25° to 50° C., preferably between 33° to 40° C., most preferably at 37° C., for periods of between 10 minutes to 3 hours, preferably between 30 minutes to 1 hour, most preferably 45 minutes. The cells are passed through a nylon or cheesecloth mesh filter of between 20 microns to 800 microns, more preferably between 40 to 400 microns, most preferably 70 microns. The cells are then subjected to differential centrifugation directly in media or over a Ficoll or Percoll or other particulate gradient. Cells will be centrifuged at speeds of between 100 to 3000×g, more preferably 200 to 1500×g, most preferably at 500×g for periods of between 1 minutes to 1 hour, more preferably 2 to 15 minutes, most preferably 5 minutes, at temperatures of between 4° to 50° C., preferably between 20° to 40° C., most preferably at about 25° C.

The invention comprises the treatment of the adipose tissue derived stromal cells to induce them to form hematopoietic, neuronal, astroglial, hepatic or other lineages of cells. While the invention is not bound by any theory of operation, it is believed that treatment of the preadipocytes with a medium containing a combination of serum, embryonic extracts, preferably a non-human embryonic extract, purified or recombinant growth factors, cytokines, hormones, and/or chemical agents, in a 2-dimensional or 3-dimensional microenvironment, will induce differentiation.

Non-limiting examples of base media useful in the methods of the invention include Minimum Essential Medium Eagle, ADC-1, LPM (Bovine Serum Albumin-free), F10 (HAM), F12 (HAM), DCCM1, DCCM2, RPMI 1640, BGJ Medium (with and without Fitton-Jackson Modification), Basal Medium Eagle (BME-with the addition of Earle's salt base), Dulbecco's Modified Eagle Medium (DMEM-without serum), Yamane, IMEM-20, Glasgow Modification Eagle Medium (GMEM), Leibovitz L-15 Medium, McCoy's 5A Medium, Medium M199 (M199E-with Earle's sale base), Medium M199 (M199H-with Hank's salt base), Minimum Essential Medium Eagle (MEM-E-with Earle's salt base), Minimum Essential Medium Eagle (MEM-H-with Hank's salt base) and Minimum Essential Medium Eagle (MEM-NAA with non essential amino acids), among numerous others, including medium 199, CMRL 1415, CMRL 1969, CMRL 1066, NCTC 135, MB 75261, MAB 8713, DM 145, Williams' G, Neuman & Tytell, Higuchi, MCDB 301, MCDB 202, MCDB 501, MCDB 401, MCDB 411, MDBC 153. A preferred medium for use in the present invention is DMEM. These and other useful media are available from GIBCO, Grand Island, N.Y., USA and Biological Industries, Bet HaEmek, Israel, among others. A number of these media are summarized in Methods in Enzymology, Volume LVIII, "Cell Culture", pp. 62–72, edited by William B. Jakoby and Ira H. Pastan, published by Academic Press, Inc.

Additional non-limiting examples of media useful in the methods of the invention can contain fetal serum of bovine or other species at a concentration of at least 1% to about 30%, preferably at least about 5% to 15%, mostly preferably about 10%. Embryonic extract of chicken or other species can be present at a concentration of about 1% to 30%, preferably at least about 5% to 15%, most preferably about 10%.

By "growth factors, cytokines, hormones" is intended the following specific factors including, but not limited to, growth hormone, erythropoeitin, thrombopoietin, interleukin 3, interleukin 6, interleukin 7, macrophage colony stimulating factor, c-kit ligand/stem cell factor, osteoprotegerin ligand, insulin, insulin like growth factors, epidermal growth factor, fibroblast growth factor, nerve growth factor, cilary neurotrophic factor, platelet derived growth factor, and bone morphogenetic protein at concentrations of between pigogram/ml to milligram/ml levels. At such concentrations, the growth factors, cytokines and hormones useful in the methods of the invention are able to induce, up to 100% the formation of blood cells (lymphoid, erythroid, myeloid or platelet lineages) from adipose derived stromal cells in colony forming unit (CFU) assays. (Moore et al. (1973) *J. Natl. Cancer Inst.* 50:603–623; Lee et al. (1989) *J. Immunol.* 142:3875–3883; Medina et al. (2993) *J. Exp. Med.* 178: 1507–1515.

It is further recognized that additional components may be added to the culture medium. Such components may be antibiotics, antimycotics, albumin, amino acids, and other components known to the art for the culture of cells. Additionally, components may be added to enhance the differentiation process.

By "chemical agents" is meant to include, but not be limited to, antioxidant compounds such as butylated hydroxyanisole (BHA) or 2-mercaptoethanol, steroids, retinoids, and other chemical compounds or agents that induce the differentiation of adipose derived stromal cells.

By "characterization" of the resulting differentiated cells is intended the identification of surface and intracellular proteins, genes, and/or other markers indicative of the lineage commitment of the stromal cells to a particular terminal differentiated state. These methods will include, but are not limited to, (a) detection of cell surface proteins by immuno-fluorescent methods using protein specific monoclonal antibodies linked using a secondary fluorescent tag, including the use of flow cytometric methods; (b) detection of intracellular proteins by immunofluorescent methods using protein specific monoclonal antibodies linked using a secondary fluorescent tag, including the use of flow cytometric methods; (c) detection of cell genes by polymerase chain reaction, in situ hybridization, and/or northern blot analysis.

Partially or terminally differentiated cells may be characterized by the identification of surface and intracellular proteins, genes, and/or other markers indicative of the lineage commitment of the stromal cells to a particular terminal differentiated state. These methods will include, but are not limited to, (a) detection of cell surface proteins by immunofluorescent assays such as flow cytometry or in situ immunostaining of adipose-derived stromal cells surface proteins such as alkaline phosphatase, CD44, CD146, integrin beta 1 or osteopontin (Gronthos et al. (1994) *Blood* 84:4164–4173); (b) detection of intracellular proteins by immunofluorescent methods such as flow cytometry or in situ immunostaining of adipose tissue-derived stromal cells using specific monoclonal antibodies directed against peroxisome proliferator activated receptors, retinoid X receptors, vitamin D receptors or Cbfal; (c) detection of the expression of lineage selective mRNAs such as osteocalcin, PPAR gamma, leptin, Cbfal, interleukin 7, osteoprotegerin ligand and/or macrophage colony stimulating factor, leukocyte marker and growth factor by methods such as polymerase chain reaction, in situ hybridization, and/or other blot analysis (See Gimble et al. (1989) *Blood* 74:303–311).

The cells may be administered into a host in order in a wide variety of ways. Preferred modes of administration are parenteral, intraperitoneal, intravenous, intradermal, epidural, intraspinal, intrasternal, intra-articular, intra-synovial, intrathecal, intra-arterial, intracardiac, intramuscular, intranasal, subcutaneous, intraorbital, intracapsular, topical, transdermal patch, via rectal, vaginal or urethral administration including via suppository, percutaneous, nasal spray, surgical implant, internal surgical paint, infusion pump, or via catheter. In one embodiment, the agent and carrier are administered in a slow release formulation such as a direct tissue injection or bolus, implant, microparticle, microsphere, nanoparticle or nanosphere.

The presence of the differentiated cells of the invention may be detected in a subject by a variety of techniques including, but not limited to, flow cytometirc, immunohistochemical, in situ hybridization, and/or other histologic or cellular biologic techniques. See, for example, Kopen etal., (1999) *Proc Natl Acad Sci* 96:10711–10716.

These cells find use in regenerating the hematopoietic system of a host deficient in any class of hematopoietic cells; a host that is diseased and can be treated by removal of blood marrow, isolation of stem cells, and treatment with drugs or irradiation prior to re-engraftment of stem cells; producing various hematopoietic cells; detecting and evaluating growth factors relevant to stem cell self-regeneration; and the development of hematopoietic cell lineages and assaying for factors associated with hematopoietic development.

The hematopoietic cells of the invention find use in therapy for a variety of disorders. Particularly, disorders associated with blood, marrow, stem cells, etc. are of interest. The transformed cells may be used to treat or prevent HIV infection.

Disorders that can be treated by infusion of the disclosed cells include, but are not limited to, diseases resulting from a failure of a dysfunction of normal blood cell production and maturation (i.e., aplastic anemia and hypoproliferative stem cell disorders); neoplastic, malignant diseases in the hematopoietic organs (e.g., leukemia and lymphomas); broad spectrum malignant solid tumors of non-hematopoietic origin; autoimmune conditions; and genetic disorders. Such disorders include, but are not limited to diseases resulting from a failure or dysfunction of normal blood cell production and maturation hyperproliferative stem cell disorders, including aplastic anemia, pancytopenia, agranulocytosis, thrombocytopenia, red cell aplasia, Blackfan-Diamond syndrome, due to drugs, radiation, or infection, idiopathic; hematopoietic malignancies including acute lymphoblastic (lymphocytic) leukemia, chronic lymphocytic leukemia, acute myelogenous leukemia, chronic myelogenous leukemia, acute malignant myelosclerosis, multiple myeloma, polycythemia vera, agnogenic myelometaplasia, Waldenstrom's macroglobulinemia, Hodgkin's lymphoma, non-Hodgkin's lymphoma; immunosuppression in patients with malignant, solid tumors including malignant melanoma, carcinoma of the stomach, ovarian carcinoma, breast carcinoma, small cell lung carcinoma, retinoblastoma, testicular carcinoma, glioblastoma, rhabdomyosarcoma, neuroblastoma, Ewing's sarcoma, lymphoma; autoimmune diseases including rheumatoid arthritis, diabetes type I, chronic hepatitis, multiple sclerosis, systemic lupus erythematosus; genetic (congenital) disorders including anemias, familial aplastic, Fanconi's syndrome, dihydrofolate reductase deficiencies, formamino transferase deficiency, Lesch-Nyhan syndrome, congenital dyserythropoietic syndrome I-IV, Chwachmann-Diamond syndrome, dihydrofolate reductase deficiencies, formamino transferase deficiency, Lesch-Nyhan syndrome, congenital spherocytosis, congenital elliptocytosis, congenital stomatocytosis, congenital Rh null disease, paroxysmal nocturnal hemoglobinuria, G6PD (glucose-6-phhosphate dehydrogenase) variants 1, 2, 3, pyruvate kinase deficiency, congenital erythropoietin sensitivity, deficiency, sickle cell disease and trait, thalassemia alpha, beta, gamma, met-hemoglobinemia, congenital disorders of immunity, severe combined immunodeficiency disease (SCID), bare lymphocyte syndrome, ionophore-responsive combined immunodeficiency, combined immunodeficiency with a capping abnormality, nucleoside phosphorylase deficiency, granulocyte actin deficiency, infantile agranulocytosis, Gaucher's disease, adenosine deaminase deficiency, Kostmann's syndrome, reticular dysgenesis, congenital Leukocyte dysfunction syndromes; and others such as osteoporosis, myelosclerosis, acquired hemolytic anemias, acquired immunodeficiencies, infectious disorders causing primary or secondary immunodeficiencies, bacterial infections (e.g., Brucellosis, Listerosis, tuberculosis, leprosy), parasitic infections (e.g., malaria, Leishmaniasis), fungal infections, disorders involving disproportionsin lymphoid cell sets and impaired immune functions due to aging, phagocyte disorders, Kostmann's agranulocytosis, chronic granulomatous disease, Chediak-Higachi syndrome, neutrophil actin deficiency, neutrophil membrane GP-180 deficiency, metabolic storage diseases, mucopolysaccharidoses, mucolipidoses, miscellaneous disorders involving immune mechanisms, Wiskott-Aldrich Syndrome, alpha 1-antirypsin deficiency, etc.

Diseases or pathologies include neurodegenerative diseases, hepatodegenerative diseases, nephrodegenerative disease, spinal cord injury, head trauma or surgery, viral infections that result in tissue, organ, or gland degeneration, and the like. Such neurodegenerative diseases include but are not limited to, AIDS dementia complex; demyeliriating diseases, such as multiple sclerosis and acute transferase myelitis; extrapyramidal and cerebellar disorders, such as lesions of the ecorticospinal system; disorders of the basal ganglia or cerebellar disorders; hyperkinetic movement disorders, such as Huntington's Chorea and senile chorea; drug-induced movement disorders, such as those induced by drugs that block CNS dopamine receptors; hypokinetic movement disorders, such as Parkinson's disease; progressive supra-nucleo palsy; structural lesions of the cerebellum; spinocerebellar degenerations, such as spinal ataxia, Friedreich's ataxia, cerebellar cortical degenerations, multiple systems degenerations (Mencel, Dejerine Thomas, Shi-Drager, and Machado-Joseph), systermioc disorders, such as Rufsum's disease, abetalipoprotemia, ataxia, telangiectasia; and mitochondrial multi-system disorder; demyelinating core disorders, such as multiple sclerosis, acute transverse myelitis; and disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Demetia of Lewy body type; Wernicke-Korsakoff syndrome; chronic alcoholism; Creutzfeldt-Jakob disease; Subacute sclerosing panencephalitis hallerrorden-Spatz disease; and Dementia pugilistica. See, e.g., Berkow et. al., (eds.) (1987), The Merck Manual, (15$^{th}$) ed.), Merck and Co., Rahway, N.J., which reference, and references cited therein, are entirely incorporated herein by reference.

In another embodiment, the adipose-derived cells can be genetically modified, e.g., to express exogenous genes or to repress the expression of endogenous genes. In accordance with this embodiment, the cell is exposed to a gene transfer vector comprising a nucleic acid including a transgene, such that the nucleic acid is introduced into the cell under conditions appropriate for the transgene to be expressed within the cell. The transgene generally is an expression cassette, including a coding polynucleotide operably linked to a suitable promoter. The coding polynucleotide can encode a protein, or it can encode biologically active RNA, such as antisene RNA or a ribozyme. Thus, the coding polynucleotide can encode a gene conferring, for example, resistance to a toxin, a hormone (such as peptide growth hormones, hormone releasing factor, sex hormones, adreno-corticotrophic hormones, cytokines such as interferons, interleukins, and lymphokines), a cell surface-bound intracellular signaling moiety such as cell-adhesion molecules and hormone receptors, and factors promoting a given lineage of differentiation, or any other transgene with known sequence.

The expression cassette containing the transgene should be incorporated into the genetic vector suitable for delivering the transgene to the cell. Depending on the desired end application, any such vector can be so employed to genetically modify the cells (e.g., plasmids, naked DNA, viruses such as adenovirus, adeno-associated virus, herpesvirus, lentivirus, papillomavirus, retroviruses, etc.). Any method of constructing the desired expression cassette within such vectors can be employed, many of which are well known in the art, such as by direct cloning, homologous recombination, etc. The desired vector will largely determine the method used to introduce the vector into the cells, which are generally known in the art. Suitable techniques include protoplast fusion, calcium-phosphate precipitation, gene gun, electroporation, and infection with viral vectors.

The cells described herein can be used in combination with any known technique of tissue engineering, including but not limited to those technologies described in patents and publications cited in the Background of the Invention (including U.S. Pat. Nos. 5,902,741 and 5,863,531 to Advanced Tissue Sciences, Inc.) as well as, but not limited to: U.S. Pat. No. 6,139,574, Vacanti et al. (Oct. 31, 2000) Vascularized Tissue Regeneration Matrices Formed By Solid Free Form Fabrication Techniques; U.S. Pat. No. 5,759,830, Vacanti et al. (Jun. 2, 1998) Three-Dimensional Fibrous Scaffold Containing Attached Cells For Producing Vascularized Tissue In Vivo; U.S. Pat. No. 5,741,685, Vacanti, (Apr. 21. 1998) Parenchymal Cells Packaged In Inmunoprotective Tissue For Implantation; U.S. Pat. No. 5,736,372, Vacanti et al. (Apr. 7, 1998) Biodegradable Synthetic Polymeric Fibrous Matrix Containing Chondrocyte For In Vivo Production Of A Cartilaginous Structure; U.S. Pat. No. 5,804,178, Vacanti et al. (Sep. 8, 1998) Implantation Of Cell-Matrix Structure Adjacent Mesentery, Omentum Or Peritoneum Tissue; U.S. Pat. No. 5,770,417, Vacanti et al. (Jun. 23. 1998) Three-Dimensional Fibrous Scaffold Containing Attached Cells For Producing Vascularized Tissue In Vivo; U.S. Pat. No. 5,770,193, Vacanti et al. (Jun. 23. 1998) Preparation of Three-Dimensional Fibrous Scaffold For Attaching Cells To Produce Vascularized Tissue In Vivo; U.S. Pat. No. 5,709,854, Griffith-Cima et al. (Jan. 20, 1998) Tissue Formation By Injecting A Cell-Polymeric Solution That Gels In Vivo; U.S. Pat. No. 5,516,532, Atala et al. (May 14, 1998) Injectable Non-Immunogenic Cartilage And Bone Preparation; U.S. Pat. No. 5,855,610, Vacanti et al. (Jan. 5. 1999) Engineering Of Strong, Pliable Tissues; U.S. Pat. No. 5,041,138, Vacanti et al. (Aug. 20, 1991) Neomorphogenesis Of Cartilage In Vivo From Cell Culture; U.S. Pat. No. 6,027,744, Vacanti et al. (Feb. 22, 1900) Guided Development and Support Of Hydrogel-Cell Compositions; U.S. Pat. No. 6,123,727, Vacanti et al. (Sep. 26, 2000) Tissue Engineered Tendons And Ligament; U.S. Pat. No. 5,536,656, Kemp et al. (Jul. 16, 1996) Preparation Of Tissue Equivalents By Contraction Of A Collagen Gel Layered On A Collagen Gel; U.S. Pat. No. 5,144,016, Skjak-Braek et al. (Sep. 1, 1992) Alginate Gels; U.S. Pat. No. 5,944,754, Vacanti (Aug. 31, 1999) Tissue Re-Surfacing With Hydrogel-Cell Compositions; U.S. Pat. No. 5,723,331, Tubo et al. (Mar. 3, 1998) Methods And Compositions For The Repair Of Articular Cartilage Defects In Mammals; U.S. Pat. No. 6,143,501, Sittinger et al. (Nov. 7, 2000) Artificial Tissues, Methods For The Production And The Use Thereof.

The present invention now will be described more fully by the following examples. This invention may, however, be embodied in many different forms and should not be construed as limited to the embodiments set forth herein; rather, these embodiments are provided so that this disclosure will be thorough and complete, and will fully convey the scope of the invention to those skilled in the art.

EXAMPLES

Example 1

Hematopoietic Commitment by Adipose Tissue-Derived Stromal Cells

A. Stromal cells are isolated from human adipose tissue according to the methods described in U.S. patent application Ser. No. 09/240,029, filed Jan. 29, 1999 now U.S. Pat. No. 6.153,432 (the contents of which are incorporated by reference), and using the modifications to the growth medium as described above. Briefly, human preadipocytes were isolated from adipose tissue removed by liposuction surgery according to the procedures previously described by Rodbell and Hauner (Rodbell (1967) and (1974); Hauner, supra). Preadipocytes from the stromal-vascular fraction were resuspended in DMEM (high glucose) media containing 10% fetal bovine serum, 5% chick embryo extract, and antibiotics and plated at 25,000 cells/well in each of the wells of a 96 well plate (150 μl/well). The cells were then placed in a 37% C 5% $CO_2$ incubator and allowed to settle overnight. The cells are cultured as primary cultures for a period of up to 5 days following initial plating. Cells are harvested by trypsin/EDTA digestion prior to differentiation/implantation.

Human adipose tissue-derived stromal cells are tested for hematopoietic differentiation based on a bone marrow repopulation assay. Immunodeficient SCID or nude/beige mice are lethally irradiated with 11 Gy of γ-irradiation in a split dose and maintained on a diet of acidified water and autoclaved food. Hematopoietic cells from the bone marrow the same animals are isolated at quantities of approximately $10^7$ cells per transplant Hematopoietic cells of murine origin ($10^7$ bone marrow derived cells) or stromal cell human origin ($10^6$ adipose derived cells) are introduced into the mice 16 hours following the lethal irradiation by injection through the tail vein or retro-orbital vein. Alternatively, the human stromal cells are mixed with the murine hematopoietic cells at a ratio of approximately 1:10 prior to transplantation into a sublethally irradiated host animal to determine a competitive repopulation assay. Animals are transfused under methoxyflurane anesthesia. Six to twelve weeks following transplantation, blood is collected from the recipient animals and subjected to flow cytometric analysis with specific monoclonal antibodies for human hematopoietic cell markers including, but not limited to, Thy 1 (T cell marker), B220 (B cell marker), Mac 1 (macrophage marker), and HLA (H-2K, human marker). The percentage of total peripheral hematopoietic cells of human versus murine origin is determined. In similar studies, bone marrow and spleen from recipient mice are harvested and subjected to in vitro clonogenic assays for specific hematopoietic lineages. These studies utilize methylcellulose colony based assays. Cells are analyzed using comparable immunofluorescent methods for specific lineage commitment.

B. Human adipose tissue from an individual human patient is isolated by liposuction and adipose-derived stromal cells isolated in vitro according tot he methods described above. The cells are cultured as primary cultures for a period of up to 5 days following initial plating in DMEM (high glucose) media containing 10% fetal bovine serum, 5% chick embryo extract, and antibiotics at 37° C. Cells are harvested by trypsin/EDTA digestion prior to differentiation/implantation.

Cells are used immediately for patients with hematopoietic disorders, such as that following high dose chemotherapy, or cryopreserved for future use in the event of an acute medical need by that patient or a histocompatible recipient. Stromal cells are infused into the recipient whether as an autologous or allogeneic transplantation, following any event such as chemotherapy or irradiation that severely compromises bone marrow function and immune competence. Stromal stem cells are marked with a fluorescent label to allow the physician to follow their fate following transplantation. Evidence of accelerated bone marrow recovery is monitored based on detection of newly synthesized hematopoietic cells (lymphoid cells, myeloid cells, erythroid cells, and platelets) in the peripheral blood stream based on flow cytometric methods.

Example 2

Astroglial Commitment by Human Adipose Tissue-Derived Stromal Cells

A. Stromal cells are isolated from human adipose tissue according to the methods described above. The cells are cultured as primary cultures for a period of up to 5 days following initial plating in a medium composed of, but not limited to, DMEM (high glucose) media containing 10% fetal bovine serum, 5% chick embryo extract, and antibiotics at 37° C. Cells are harvested by trypsin/EDTA digestion prior to differentiation/implantation.

Cells are transplanted into the central nervous system of immunodeficient mice or rats. Nude/beige or SCID mice or nude rats are anesthetized in a sealed chamber using 3% halothane in oxygen; anesthesia is maintained by intramuscular injection of 6 mg/kg of xylozine and 60 mg/kg of ketamine. The animals are transferred to a sterotaxic apparatus in a clean field. A 2-to-5-mm incision is made in the scalp 2 mm lateral to the bregma. A burr hole is made in the bone 3 mm lateral to the bregma with a dental drill. Approximately 10 µl of cell suspension (10,000 cells per µl) is injected slowly over a 30-minute period into the striatum at a depth of 4–5 mm from the surface of the brain. The wound is sutured close and the animals followed for a period of up to 10 weeks. Animals are euthanized by intracardia perfusion following deep anesthesia with xylozine and ketamine, using ice cold PBS, 3% buffered paraformaldehyde, and then 10% sucrose. The brains are examined by immunohistochemistry and in situ hybridization for the presence of human gene markers (Alu fragment) and expression of cell lineage specific markers. Evidence of human cell survival, differentiation, and migration is determined by this approach. Modifications using cell labeling with fluorescent dyes or genetic engineering of the cells prior to implantation with viral agents can be considered.

B. Stromal cells are isolated from human adipose tissue according of an individual patient for autologous or allogeneic transplantation to a histocompatible recipient according to the methods described above. The cells are cultured as primary cultures for a period of up to 5 days following initial plating in a medium composed of, but not limited to, DMEM (high glucose) media containing 10% fetal bovine serum, 5% chick embryo extract, and antibiotics at 37° C. Cells are harvested by trypsin/EDTA digestion prior to differentiation/implantation.

Stromal cells will be introduced into the central nervous system of a patient following a life-threatening and/or debilitating central nervous system disorder or disease, such as a craniovascular accident (stroke), Parkinson's disease, or Alzheimer's disease. Cells are infused into the striatum of the affected area of the brain using a neurosurgical approach. Wherever possible, radiologically guided, minimally invasive methods are used. Cognitive and metabolic function of the central nervous system are followed after the surgery to document improvements secondary to transplantation. Cells are genetically engineered with genes encoding enzymes designed to improve CNS function, such as dopamine metabolic enzymes in the case of Parkinson's disease, are used as appropriate to particular disorders.

Example 3

Neuronal Commitment by Human Adipose Tissue-Derived Stromal Cells: Improved Repair and Functional Recovery in a Traumatic Nervous System Injury Stromal cells are isolated from human adipose tissue according of an individual patient for autologous or allogeneic transplantation to a histocompatible recipient according to the methods described above. The cells are cultured as primary cultures for a period of up to 5 days following initial plating in a medium composed of, but not limited to, DMEM (high glucose) media with 1 mM glutamine but without pyruvate, containing 10% fetal bovine serum, 10% newborn calf serum, nucleoside stocks, 0.1 mM 2-mercaptoethanol, 1000 units/ml of leukemia inhibitory factor and antibiotics at 37° C.

Cells are harvested by trypsin/EDTA digestion prior to differentiation/implantation. Cells are then plated on tissue culture plastic substrate coated with 0.1% sterile gelatin solution. Cells are harvested during rapid growth stage by 0.25% trypsin and 1 mM EDTA digestion and trituration prior to differentiation/implantation. Cells are harvested as a suspension, with single cell and cell clumps together. Cells are aliquoted to 100 mm diameter bacteriological (nontissue culture) dishes in a volume of 10 ml of medium consisting of DMEM (high glucose) media with 1 mM glutamine but without pyruvate, containing 10% fetal bovine serum, 10% newborn calf serum, and nucleoside stocks (control medium). The cell cultures are maintained for 2 days, during which time cell aggregates form; at this time, medium is replaced with the original control medium. After an additional 2 days in culture (day 4 after passage), the cells are fed with control medium supplemented with all-trans retinoic acid at concentrations of between $10^{-9}$ M to $10^{-6}$ M, most preferably at $5 \times 10^{-7}$ M. The cells are maintained in the all trans retinoic acid supplemented medium on day 6. On day 8 after passage, the cells are ready for evaluation and use in the treatment of a spinal or peripheral nervous system traumatic injury model.

In vitro evaluation of the cells is performed by passing the cells from the bacteriological culture dish to standard tissue culture dishes to provide a substrate for attachment. Cells are allowed to adhere to the plastic and evaluated based on their morphology, consistent with a neuronal differentiation profile, and on their expression of neuronal associated proteins, including but not limited to, class III beta-tubulin, the M subunit of neurofiliments, tyrosine hydroxylase, gluatmate receptor subunits of the GluR1–4 and GluR6 classes, glial fibrillary acidic protein, myelin basic protein, and brain factor 1 (Bain et al. (1995) *Develop. Biol.* 168:342–357).

In vivo evaluation of the cells is performed by transplanting the cell aggregates into the syrinx that forms around an experimentally induced thoracic spinal cord lesion in rats (McDonald et al. (1999) *Nature Med.* 5(12):1410–1412). The thoracic spinal cord injury model (thoracic vertebra 9–10) is created in Long-Evans rats using a 10 gram rod 2.5 mm in diameter falling 25 mm. On the ninth day after the injury, adipose tissue-derived stromal cell aggregates (approximately $10^{-6}$ cells) are transplanted by injection using a microstereotaxic injection system into the syrinx of the thoracic spinal cord injury. Sham operated controls are injected with an equivalent volume of media alone (no cells). Beginning on the day of transplantation, rats receive cyclosporine daily (10 mg/kg) to prevent rejection. Hindlimb motor function is assessed based on the Basso-Beattie-Breesnahan Locomotor Rating Scale in the rats over a 6 week period following transplantation to allow functional comparison of the recovery between stromal cell transplanted and sham operated controls. At the conclusion of the study (6 weeks), animals are sacrificed and the tissues examined histologically for evidence of human adipose stromal cells are detected based on in situ detection of the human Alu DNA. Cell differentiation is determined by antibody detection of oligodendrocyte specific markers such as, but not exclusively, adenomatous polyposis coli gene product APC CC-1, astrocyte specific markers such as, but not exclusively, glial fibrillary acidic protein, GFAP, and neuronal such as, but not exclusively, neuron-specific nuclear protein, NeuN. Colocalization of the Alu DNA with differentiation specific markers is taken as evidence of stromal cell differentiation.

Alternatively, the isolated adipose tissue derived stromal cells are cultured as primary cultures for a period of up to 5 days following initial plating in a medium composed of, but not limited to, DMEM (high glucose) media containing 10% fetal bovine serum, 5% chick embryo extract, and antibiotics at 37° C. Cells are harvested by trypsin/EDTA digestion prior to differentiation/implantation.

Human adipose tissue-derived stromal cells are tested for neuronal differentiation based on in vitro assays. Human adipose tissue-derived stromal cells are cultured at concentrations of 8,000 cells/cm$^2$ for 24 hours in DMEM supplemented with 20% fetal bovine serum and antibiotics. The cells are then treated with antioxidants such as BHA at concentrations of 20 µM to 200 µM in DMEM with 0% fetal bovine serum for periods of 5 hours to 5 days. Cells are fixed and examined for the expression of neuronal differentiation by (a) morphological criteria; (b) immunohistochemical, immunofluorescent or flow cytometric criteria; (c) immunoblot criteria; and/or (d) polymerase chain reaction or northern blot analysis of selected mRNAs. Cells are assessed for their expression of a subset of the following neuronal markers: NeuN, NF-M, NSE, nestin, and trkA using antibody or oligonucleotide reagents. Morphologic criteria of differentiation include the formation of a contracted multipolar cell body with membranous, process-like cell extensions leading to growth cone-like termini and filopodial extensions, the ability of such cells to generate and maintain an action potential consistent with neuronal signal transmission, and the ability to express receptors and uptake systems for known neurotransmitters, such as the glutamate.

Example 4

Hepatocyte Commitment by Human Adipose Tissue-Derived Stromal Cells

A. Stromal cells are isolated from human adipose tissue according to the methods described in "Methods and Composition for the Differentiation of Human Preadipocytes into Adipocytes" Ser. No. 09/240,029 filed Jan. 29, 1999. now U.S. Pat. No. 6,153.432, and using the modifications listed above. The cells are cultured as primary cultures for a period of up to 5 days following initial plating in a medium composed of, but not limited to, DMEM (high glucose) media containing 10% fetal bovine serum, 5% chick embryo extract, and antibiotics at 37° C. Cells will be harvested by trypsin/EDTA digestion prior to differentiation/implantation.

Adipose tissue-derived stromal cells are transplanted into immunodeficient nude mice carrying a transgene for the mouse major urinary protein-urokinase-type plasminogen activator fusion gene [Weglarz TC, Degen JL, Sandgren EP 2000 Hepatocyte transplantation into diseased mouse liver: kinetics of parenchymal repopulation and identification of the proliferative capacity of tetraploid and octaploid hepatocytes. Am J Pathol 157:1963–1974]. These animals exhibit a progressive degeneration of the liver. The stromal cells are introduced into the animal model by transplantation into the spleen, intraperitoneal, and/or intravenous infusion. Representative animals from control or experimental groups are sacrificed at intervals over a 4 month time course. Evidence of liver regeneration will be assessed based on histologic and molecular biological analyses of the liver tissue. Immunohistochemical and molecular biological (Alu staining) methods will document the presence of human cells in the regenerated liver.

B. Stromal cells will be isolated from human adipose tissue according of an individual patient for autologous or allogeneic transplantation to a histocompatible recipient according to the methods described in "Methods and Composition for the Differentiation of Human Preadipocytes into Adipocytes" Ser. No. 09/240,029 filed Jan. 29, 1999 now U.S. Pat. No. 6.153,432, and using the modifications listed above. The cells are cultured as primary cultures for a period of up to 5 days following initial plating in a medium composed of, but not limited to, DMEM (high glucose) media containing 10% fetal bovine serum, 5% chick embryo extract, and antibiotics at 37° C. Cells will be harvested by trypsin/EDTA digestion prior to differentiation/implantation.

Stromal cells will be introduced into the spleen, circulation, and/or peritoneum of a patient suffering from degenerative liver diseases of any origin, secondary to viral infection, toxin ingestion, or inborn metabolic errors. Wherever possible, radiologically guided, minimally invasive methods will be used to implant the cells. Cells genetically engineered with genes encoding enzymes designed to improve hepatic function will be used as appropriate to particular disorders.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims.

Although specific terms are employed herein, they are used in a generic and descriptive sense only and not for purposes of limitation.

We claim:

1. An isolated adipose tissue-derived stromal cell that has been differentiated and expresses at least one neuronal marker of a neuronal cell, wherein the neuronal marker is selected from the group consisting of neuron-specific protein (NeuN), neurofilament medium polypeptide (NF-M), neuron-specific enolase (NSE), nestin, trkA, class III beta-tubulin, M subunit of neurofilaments, tyrosine hydroxylase, glutamate receptor subunits of the GluR1–4 and GluR6 classes, glial fibrillary acidic protein, myelin basic protein, and brain factor 1.

2. An isolated adipose tissue-derived stromal cell that has been differentiated to exhibit at least one characteristic of a neuronal cell, wherein at least one characteristic is a process-like cell extension.

* * * * *